United States Patent
Mauer et al.

(10) Patent No.: US 10,463,888 B2
(45) Date of Patent: Nov. 5, 2019

(54) SHAMPOOS AND CONDITIONERS HAVING A CONDITIONING EFFECT

(71) Applicant: BASF SE, Ludwigshafen (DE)

(72) Inventors: Werner Mauer, Sendenhorst-Albersloh (DE); Werner Seipel, Hilden (DE); Hans-Martin Haake, Erkrath (DE); Sybille Cornelsen, Ratingen (DE); Guadalupe Pellon, Duesseldorf (DE); Birgit Glasmacher, Dusseldorf (DE); Helga Gondek, Duesseldorf (DE)

(73) Assignee: BASF SE, Ludwigshafen (DE)

( * ) Notice: Subject to any disclaimer, the term of this patent is extended or adjusted under 35 U.S.C. 154(b) by 55 days.

(21) Appl. No.: 15/525,599

(22) PCT Filed: Nov. 3, 2015

(86) PCT No.: PCT/EP2015/075551
§ 371 (c)(1),
(2) Date: May 10, 2017

(87) PCT Pub. No.: WO2016/074986
PCT Pub. Date: May 19, 2016

(65) Prior Publication Data
US 2017/0333734 A1    Nov. 23, 2017

(30) Foreign Application Priority Data
Nov. 13, 2014 (EP) .................................. 14193046

(51) Int. Cl.
| *A61K 8/00* | (2006.01) |
| *A61Q 5/02* | (2006.01) |
| *A61K 8/37* | (2006.01) |
| *A61K 8/46* | (2006.01) |
| *A61K 8/73* | (2006.01) |
| *A61K 8/92* | (2006.01) |

(52) U.S. Cl.
CPC ................ *A61Q 5/02* (2013.01); *A61K 8/375* (2013.01); *A61K 8/463* (2013.01); *A61K 8/466* (2013.01); *A61K 8/731* (2013.01); *A61K 8/737* (2013.01); *A61K 8/922* (2013.01)

(58) Field of Classification Search
None
See application file for complete search history.

(56) References Cited

U.S. PATENT DOCUMENTS

| 4,172,887 A | 10/1979 | Vanlerberghe et al. |
| 2007/0292383 A1 | 12/2007 | Schepky et al. |
| 2010/0183536 A1 | 7/2010 | Ansmann et al. |
| 2011/0124542 A1 | 5/2011 | Sartingen |
| 2016/0045417 A1* | 2/2016 | Schroeder ................ A61K 8/42 132/202 |

FOREIGN PATENT DOCUMENTS

| DE | 102008034388 A1 | 1/2010 |
| FR | 2252840 A1 | 6/1975 |
| WO | WO-00/64410 A1 | 11/2000 |
| WO | WO-2005/048971 A1 | 6/2005 |
| WO | WO-2008/155073 A2 | 12/2008 |
| WO | WO-2013/007473 A2 | 1/2013 |
| WO | WO-2014/177292 A1 | 11/2014 |

OTHER PUBLICATIONS

Extended European Search Report for EP Patent Application No. 14193046.1, dated May 7, 2015 (9 pages).
International Search Report and Written Opinion for PCT Application No. PCT/EP2015/075551, dated Dec. 2, 2015 (14 pages).
Database GNPD Mintel, "L'Occitane en Provence Aromachologie 5 essential oils," XP002738731, Database Accession No. 1363498, Jul. 30, 2010.
International Preliminary Report on Patentability for PCT Patent Application No. PCT/EP2015/075551, dated May 26, 2017 (19 pages).

* cited by examiner

*Primary Examiner* — Necholus Ogden, Jr.
(74) *Attorney, Agent, or Firm* — Marshall, Gerstein & Borun LLP

(57) ABSTRACT

The present invention relates to a composition suitable as a shampoo or hair conditioner, comprising at least one surfactant, at least one cationic polymer, ethoxylated fatty acid glycerides, ethoxylated mono- and diglycerol esters, trimethylpropane EO/PO trioleate, NaCl and water. The present invention further relates to an intermediate suitable for preparing said composition, comprising ethoxylated fatty acid glycerides, ethoxylated mono- and diglycerol esters and trimethylpropane EO/PO trioleate.

16 Claims, No Drawings

SHAMPOOS AND CONDITIONERS HAVING A CONDITIONING EFFECT

CROSS-REFERENCE TO RELATED APPLICATIONS

This application is the U.S. National Phase of PCT/EP2015/075551, filed Nov. 3, 2015, which claims the benefit of European Patent Application No. 14193046.1, filed Nov. 13, 2014.

The present invention relates to a composition suitable as a shampoo or hair conditioner, comprising at least one surfactant, at least one cationic polymer, ethoxylated fatty acid glycerides, ethoxylated mono- and diglycerol esters, trimethylpropane EO/PO trioleate, NaCl and water. The present invention further relates to an intermediate suitable for preparing said composition, comprising ethoxylated fatty acid glycerides, ethoxylated mono- and diglycerol esters and trimethylpropane EO/PO trioleate.

Most shampoos currently found on the market comprise a combination of (1) an anionic surfactant, (2) a cosurfactant, (3) a cationic polymer and (4) one or more so-called emollients or waxes. Here, the emollients or waxes serve to condition the hair.

Various surfactants are used as cosurfactant (2), e.g. coco betaine, APG, amphoacetates. Therefore, betaine and nonionic surfactants among others, and optionally also anionic surfactants, are used.

The cationic polymers (3) used are, inter alia, polyquaternium-10 (abbreviated as PQ 10), cationically modified cellulose, cationic guar derivatives.

The emollients (4) used are, inter alia, native or synthetic oils or silicones.

By means of so-called coacervate formation (coacervation) (that is the precipitation of a complex of cationic polymer and anionic surfactant) on dilution (rinsing of the hair), cationic polymers and emollients/waxes are deposited on the hair. The deposited material then reduces friction on combing the wet and dry hair. This is measured as wet and dry combability. The substances used as conditioning agents are typically hydrophobic. Silicones (polysiloxanes) are often used as emollients.

Hair conditioning is understood by those skilled in the art to mean the treatment of hair with caring so-called rinse-off formulations (i.e. formulations which are rinsed off) or so-called leave-on formulations (i.e. Formulations which remain on the hair without being rinsed off), particularly with caring shampoos or conditioners. This treatment leads in particular to easier combability of the hair in the wet and dry state, both along the lengths and at the tips (detanglability), to improved tactile properties such as smoothness, softness and suppleness and also to more hair shine, less electrostatic charge and improved ease of styling. Overall, a cared-for and healthy overall condition of the hair is thus achieved by the conditioning.

In addition to the aforementioned hydrophobic substances for improving the combability, hydrophilic components such as Cetiol® HE (a coconut fatty acid mono- and diglyceride+7 mol of ethylene oxide units (abbreviated as EO below)) or Eumulgin® CO 40 (a hydrogenated castor oil having 40 mol of EO) are used as solubilizers (these are solubilizers for oils, hydrophobic substances or perfumes) in shampoos.

DE 10 2008 034 388 discloses a surfactant-containing composition comprising, in addition to one or more oil component(s), a mixture of solubilizers selected from the group of a) ethoxylated fatty alcohols, b) ethoxylated hydrogenated castor oils and c) ethoxylated mono-, di- or triglycerol esters, wherein the ratio of components a):b):c) is in the range of 1:(2-4):(3-4).

WO 00/64410 describes the improvement of wet combability by using a shampoo consisting of surfactant plus cationic polymer and/or cationic surfactant and poly-alpha-olefin oil starting from C6-16 alkene monomers.

WO 2005/048971 describes the use of hydrophilic solubilizers in formulations for body cleansing with the aim of reduced damage of enzymes on the skin.

The object of the present invention is to provide an alternative to the known shampoos or conditioners having a conditioning effect which are based on hydrophobic emollients or waxes.

Where possible, shampoos or rinses with a conditioning effect should be provided which do not necessarily have to comprise silicones since silicone-free products are currently being sought on the market.

In addition, where possible, a good conditioning effect should also be achieved, in particular also on damaged hair, which is hydrophilic due to the damage and therefore has a less strong interaction with hydrophobic care substances.

In the search for formulations for shampoos or conditioners contributing to improved combability, it has been found, surprisingly, that a combination of hydrophilic solubilizers with cationic care polymers and surfactants also resulted in a significant improvement in combability even without using hydrophobic substances.

Composition

The abovementioned object is achieved by a composition suitable as a shampoo or conditioner, comprising
 at least one surfactant,
 optionally at least one cosurfactant which is different from the at least one surfactant,
 at least one cationic polymer,
 ethoxylated fatty acid glycerides,
 ethoxylated mono- and diglycerol esters
 trimethylpropane EO/PO trioleate,
 NaCl
 optionally glycerol,
 optionally further ingredients customary in shampoos or hair conditioners, and
 water.

This composition is likewise a subject matter of the present invention.

Surfactants

The at least one surfactant present in the composition according to the invention may be any surfactant. In particular, a possible surfactant is selected from the group consisting of a sulfate, an ethoxylated sulfate, a sulfonate, an alkyl polyglycoside, a derivative of an alkyl polyglycoside, a betaine, an amphoacetate, a glutamate, a sulfosuccinate, a taurate, a glycinate and an isethionate. In one embodiment of the present invention, the at least one surfactant is an anionic surfactant, preferably a sodium alkyl ether sulfate having 12 to 14 carbon atoms and two ethylene oxide units as ether component.

In a further embodiment of the present invention, the at least one surfactant is an anionic and/or non-ionic and/or amphoteric and/or zwitterionic surfactant of which the proportion in the compositions according to the invention is preferably 3 to 40% by weight, preferably 5 to 35 and especially 10 to 30% by weight. Typical examples of anionic surfactants are soaps, alkylbenzenesulfonates, alkanesulfonates, olefin-sulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ethercarboxylic acids and salts thereof, fatty acid isethionates, fatty acid sarcosinates, fatty acid taurides, N-acylamino acids, for example acyl lactylates, acyl tartrates, acyl glutamates and acyl aspartates, alkyl oligoglucoside sulfates, protein fatty acid condensates (especially vegetable products based on wheat) and alkyl (ether) phosphates. If the anionic surfactants comprise polyglycol ether chains, these may have a conventional homolog distribution, but preferably have a narrow homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucuronic acid derivatives, fatty acid N-alkylglucamides, protein hydrolyzates (especially wheat-based vegetable products), polyol fatty acid esters, sugar esters, sorbitan esters, polysorbates and amine oxides. If the nonionic surfactants contain polyglycol ether chains, they may have a conventional homolog distribution, but preferably have a narrow homolog distribution. Typical examples of amphoteric or zwitterionic surfactants are alkyl betaines, alkylamido betaines, aminopropionates, aminoglycinates, imidazolinium betaines and sulfo betaines. The specified surfactants are exclusively known compounds.

The at least one surfactant present in the composition according to the invention is preferably present in the composition according to the invention in an amount of 10 to 20% by weight.

Cosurfactants

The at least one cosurfactant present in the composition according to the invention may be any cosurfactant. It is selected such that it is different from the at least one surfactant. In one embodiment of the present invention, the at least one surfactant is a cocamidopropylbetaine.

In one embodiment, the composition according to the present invention comprises a combination of a sodium alkyl ether sulfate having 12 to 14 carbon atoms and two ethylene oxide units as ether component as surfactant and a cocamidopropylbetaine as cosurfactant.

The at least one cosurfactant present in the composition according to the invention is preferably present in the composition according to the invention in an amount of 10 to 15% by weight.

Cationic Polymers

The at least one cationic polymer present in the composition according to the invention may be any cationic polymer. In one embodiment of the present invention, the at least one cationic polymer is selected from the group consisting of a cationically modified cellulose derivative, PQ 10, PQ 67, a cationically modified guar derivative, guar hydroxypropyltrimonium chloride, a cationic homo- or copolymer based on acrylamide, a cationic homo- or copolymer based on vinyl pyrrolidone, a cationic homo- or copolymer based on quaternized vinyl imidazole and a cationic homo- or copolymer based on methacrylates.

The at least one cationic polymer present in the composition according to the invention is preferably present in the composition according to the invention in an amount of 0.02 to 5% by weight.

Suitable cationic polymers are furthermore, for example, cationic cellulose derivatives such as a quaternized hydroxyethylcellulose, which is obtainable under the name Polymer JR 400® from Amerchol, cationic starch, copolymers of diallylammonium salts and acrylamides, quaternized vinylpyrrolidone/vinylimidazole polymers such as Luviquat® (BASF), condensation products of polyglycols and amines, quaternized collagen polypeptides such as lauryldimonium hydroxypropyl hydrolyzed collagen (Lamequat®/ Grünau), quaternized wheat polypeptides, polyethyleneimine, cationic silicon polymers such as amidomethicones, copolymers of adipic acid and dimethylaminohydroxypropyldiethylenetriamine (Cartaretine®/Sandoz), copolymers of acrylic acid with dimethyldiallylammonium chloride (Merquat® 550/Chemviron), polyaminopolyamides such as described in FR-A 2252840 and also crosslinked water-soluble polymers thereof, cationic chitin derivatives such as quaternized chitosan, optionally in microcrystalline distribution, condensation products of dihaloalkylene such as dibrombutane with bisdialkylamines such as bisdimethylamino-1,3-propane, cationic guar gum such as Jaguar® CBS, Jaguar® C-17, Jaguar® C-16 from Celanese, quaternized ammonium salt polymers such as Mirapol® A-15, Mirapol® AD-1, Mirapol® AZ-1 from Miranol.

Cationic polymers are used in the compositions according to the invention preferably in amounts of 0.02 to 5% by weight, preferably 0.05 to 3% by weight and particularly preferably in amounts of 0.1 to 2% by weight.

Ethoxylated Fatty Acid Glycerides

The ethoxylated fatty acid glycerides present in the composition according to the invention are a mixture of several individual compounds. They are obtainable by the reaction of fatty acid glycerides with ethylene oxide (EO) in alkaline conditions, in the presence of KOH for example, at elevated temperature, 100 to 150° C. for example, wherein transesterifications and ethoxylations take place such that the resulting product may also comprise ethoxylated partial glycerides. In one embodiment of the present invention, ethoxylated hydrogenated castor oils are used. In one embodiment of the present invention, ethoxylated hydrogenated castor oil having 40 ethylene oxide units is used.

In the context of the present invention, fatty acids refer in particular to aliphatic monocarboxylic acids having unbranched carbon chains, particularly those having 6 to 30 carbon atoms.

The ethoxylated fatty acid glycerides present in the composition according to the invention are present in the composition according to the invention preferably in an amount of 0.06 to 3.5% by weight, preferably 0.12 to 2.1% by weight.

Ethoxylated Mono- and Diglycerol Esters

The ethoxylated mono- and diglycerol esters present in the composition according to the invention are a mixture of several individual compounds. They are mixtures of molecules each comprising a glycerol residue and each comprising one or two fatty acid residues and each comprising a certain statistical average number of ethylene oxide residues. In one embodiment of the present invention, ethoxylated coconut oil partial glycerides are used. In one embodiment of the present invention, ethoxylated coconut oil partial glycerides having 7 ethylene oxide units are used.

The ethoxylated mono- and diglycerol esters present in the composition according to the invention are present in the composition according to the invention preferably in an amount of 0.06 to 2.5% by weight, preferably 0.12 to 1.5% by weight.

Trimethylpropane EO/PO Trioleate,

The trimethylpropane EO/PO trioleate present in the composition according to the invention is a mixture of several individual compounds. It is obtainable by the reaction of trimethylolpropane trioleate with ethylene oxide and propylene oxide under alkaline conditions. Ethylene oxide units (EO) and propylene oxide units (PO) are incorporated, at least in part, into the ester groups of the trimethylolpropane trioleate. The trimethylpropane EO/PO trioleate is characterized by the statistical average its content of EO and PO units per molecule. In one embodiment of the present invention, trimethylpropane EO/PO trioleate having 120 ethylene oxide units (EO) and 10 propylene oxide units is used.

The trimethylpropane EO/PO trioleate present in the composition according to the invention is present in the composition according to the invention preferably in an amount of 0.03 to 0.5% by weight, preferably 0.06 to 0.3% by weight.

NaCl (Common Salt)

A feature of the composition according to the invention is the presence of NaCl. This ensures that the coacervate mechanism of anionic surfactant and cationic polymer is initiated in the dilution phase. In this case, the NaCl can be entrained with the cosurfactant (cocamidopropylbetaine for example which often, by virtue of the production process, already comprises ca. 5-7.5% by weight NaCl) and/or can be added separately.

Waxes (Also Called Wax Bodies)

Suitable wax bodies in the wax dispersions are: alkylene glycol esters, fatty acid alkanolamides, partial glycerides, esters of polybasic, optionally hydroxy-substituted carboxylic acids, fatty alcohols, fatty ketones, fatty aledyhdes, fatty ethers, fatty carbonates, ring-opening products of olefin epoxides and mixtures thereof.

The alkylene glycol esters are typically mono- and/or diesters of alkylene glycols having the formula (I) below, $$R^1CO(OA)_nOR^2 \qquad (I)$$

in which $R^1CO$ is a linear or branched, saturated or unsaturated acyl radical having 6 to 22 carbon atoms, $R^2$ is hydrogen or $R^1CO$ and A is a linear or branched alkylene radical having 2 to 4 carbon atoms and n is a number from 1 to 5. Typical examples are mono- and/or diesters of ethylene glycol, propylene glycol, diethylene glycol, dipropylene glycol, triethylene glycol or tetraethylene glycol with fatty acids having 6 to 22, preferably 12 to 18 carbon atoms as: caproic acid, caprylic acid, 2-ethylhexanoic acid, capric acid, lauric acid, isotridecanoic acid, myristic acid, palmitic acid, palm oleic acid, stearic acid, isostearic acid, oleic acid, elaidic acid, petroselinic acid, linoleic acid, linolenic acid, elaeostearic acid, arachic acid, gadoleic acid, behenic acid and erucic acid and technical-grade mixtures thereof. Particular preference is given to the use of ethylene glycol monostearate and/or distearate.

Other wax bodies such as fatty acid alkanolamides, have the formula (II) below, $$R^3CO-NR^4-B-OH \qquad (II)$$

in which $R^3CO$ is a linear or branched, saturated or unsaturated acyl radical having 6 to 22 carbon atoms, $R^4$ is hydrogen or an optionally hydroxy-substituted alkyl radical having 1 to 4 carbon atoms and B is a linear or branched alkylene group having 1 to 4 carbon atoms. Typical examples are condensation products of ethanolamine, methylethanolamine, diethanolamine, propanolamine, methylpropanolamine and dipropanolamine and mixtures thereof with caproic acid, caprylic acid, 2-ethylhexanoic acid, capric acid, lauric acid, isotridecanoic acid, myristic acid, palmitic acid, palm oleic acid, stearic acid, isostearic acid, oleic acid, elaidic acid, petroselinic acid, linoleic acid, linolenic acid, elaeostearic acid, arachic acid, gadoleic acid, behenic acid and erucic acid and technical-grade mixtures thereof. Particular preference is given to using stearic acid ethanolamide.

Partial glycerides are mono and/or diesters of glycerol with linear, saturated and/or partially unsaturated fatty acids, for example, caproic acid, caprylic acid, lauric acid, myristic acid, palmitic acid, palm oleic acid, tallow fatty acid, stearic acid, behenic acid and technical-grade mixtures thereof. They are of the formula (III),

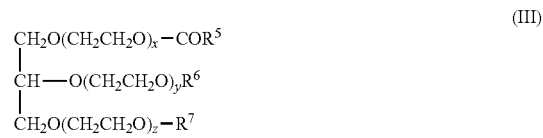

in which $R^5CO$ is an acyl radical having 6 to 22 carbon atoms, preferably a linear, saturated acyl radical having 6 to 22 carbon atoms, $R^6$ and $R^7$ are each independently hydrogen or $R^5CO$, x, y and z in total are 0 or a number from 1 to 30 and X is an alkali metal or alkaline earth metal with the proviso that at least one of the two radicals $R^6$ and $R^7$ is hydrogen. Typical examples are lauric acid monoglyceride, lauric acid diglyceride, coconut fatty acid monoglyceride, coconut fatty acid triglyceride, palmitic acid monoglyceride, palmitic acid triglyceride, stearic acid monoglyceride, stearic acid diglyceride, tallow fatty acid monoglyceride, tallow fatty acid diglyceride, behenic acid monoglyceride, behenic acid diglyceride and technical-grade mixtures thereof which may contain minor amounts of triglyceride depending on the production process.

Also suitable as wax bodies as a preferred group are esters of polybasic, optionally hydroxy-substituted carboxylic acids with fatty alcohols having 6 to 22 carbon atoms. Suitable acid components of these esters are, for example, malonic acid, maleic acid, fumaric acid, adipic acid, sebacic acid, azelaic acid, dodecanedioic acid, phthalic acid, isophthalic acid and, in particular, succinic acid and also malic acid, citric acid and in particular tartaric acid and mixtures thereof. The fatty alcohols comprise 6 to 22, preferably 12 to 18 and especially 16 to 18 carbon atoms in the alkyl chain. Typical examples are caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical-grade mixtures thereof. The esters may be present as full or partial esters, preference being given to using monoesters and especially diesters of carboxylic acids or hydroxycarboxylic acids. Typical examples are succinic acid mono- and dilauryl esters, succinic acid mono- and dicetearyl esters, succinic acid mono- and distearyl esters, tartaric acid mono- and dilauryl esters, tartaric acid mono- and dicocoalkyl esters, tartaric acid mono- and dicetearyl esters, citric acid mono-, di- and trilauryl esters, citric acid mono-, di- and tricocoalkyl esters and citric acid mono-, di- and tricetearyl esters.

As a third preferred group of wax bodies, it is possible to use fatty alcohols having the formula (IV), $$R^8OH \qquad (IV)$$

in which $R^8$ is a linear, optionally hydroxy-substituted alkyl radical and/or acyl radical having 16 to 48, preferably 18 to 36 carbon atoms. Typical examples of suitable alcohols are cetearyl alcohol, hydroxystearyl alcohol, behenyl alcohol and oxidation products of long-chain paraffin.

Fatty ketones, which are suitable as components, preferably have the formula (V),

$$R^9\text{—}CO\text{—}R^{10} \quad (V)$$

in which $R^9$ and $R^{10}$ are each independently alkyl and/or alkenyl radicals having 1 to 22 carbon atoms with the proviso that they have in total at least 24 and preferably 32 to 48 carbon atoms. The ketones may be prepared by methods according to the prior art, for example by pyrolysis of the corresponding fatty acid magnesium salts. The ketones can be symmetrical or asymmetrical, preferably the two radicals $R^{13}$ and $R^{14}$ differ only by one carbon atom and are derived from fatty acids having 16 to 22 carbon atoms.

Fatty aldehydes suitable as wax bodies preferably correspond to the formula (VI), $$R^{11}COH \quad (VI)$$

in which $R^{11}CO$ is a linear or branched acyl radical having 24 to 48, preferably 28 to 32 carbon atoms.

Likewise, suitable fatty ethers are preferably of the formula (VII),

$$R^{12}\text{—}O\text{—}R^{13} \quad (VII)$$

in which $R^{12}$ and $R^{13}$ are each independently alkyl and/or alkenyl radicals having 1 to 22 carbon atoms with the proviso that they have in total at least 24 and preferably 32 to 48 carbon atoms. Fatty ethers of the type mentioned are typically prepared by acidic condensation of the corresponding fatty alcohols. Fatty ethers with particularly advantageous pearlescent properties are obtained by condensation of fatty alcohols having 16 to 22 carbon atoms such as cetyl alcohol, cetearyl alcohol, stearyl alcohol, isostearyl alcohol, oleyl alcohol, behenyl alcohol and/or erucyl alcohol.

Suitable components are, furthermore, fatty carbonates, preferably of the formula (VIII),

$$R^{14}O\text{—}CO\text{—}OR^{15} \quad (VIII)$$

in which $R^{14}$ and $R^{15}$ are each independently alkyl and/or alkenyl radicals having 1 to 22 carbon atoms with the proviso that they have in total at least 24 and preferably 32 to 48 carbon atoms. The substances are obtained in a manner known per se by transesterifying, for example, dimethyl carbonate or diethyl carbonate with the corresponding fatty alcohols. Accordingly, the fatty carbonates may be symmetrical or asymmetrical. However, preference is given to using carbonates in which $R^{14}$ and $R^{15}$ are identical and are alkyl radicals having 16 to 22 carbon atoms. Particular preference is given to transesterification products of dimethyl carbonate or diethyl carbonate with cetyl alcohol, cetearyl alcohol, stearyl alcohol, isostearyl alcohol, oleyl alcohol, behenyl alcohol and/or erucyl alcohol in the form of their mono- and diesters or technical-grade mixtures thereof.

Epoxide ring-opening products are known substances which are prepared typically by acid-catalyzed reaction of terminal or internal olefin epoxides with aliphatic alcohols. The reaction products are preferably of the formula (IX),

in which $R^{16}$ and $R^{17}$ are hydrogen or an alkyl radical having 10 to 20 carbon atoms with the proviso that the sum total of carbon atoms of $R^{16}$ and $R^{17}$ is in the range of 10 to 20 and $R^{18}$ is an alkyl and/or alkenyl radical having 12 to 22 carbon atoms and/or is the radical of a polyol having 2 to 15 carbon atoms and 2 to 10 hydroxyl groups. Typical examples are ring-opening products of α-dodecene epoxide, α-hexadecene epoxide, α-octadecene epoxide, α-eicosene epoxide, α-docosene epoxide, i-dodecene epoxide, i-hexadecene epoxide, i-octadecene epoxide, i-eicosene epoxide and/or i-docosene epoxide with lauryl alcohol, coconut fatty alcohol, myristyl alcohol, cetyl alcohol, cetearyl alcohol, stearyl alcohol, isostearyl alcohol, oleyl alcohol, elaidyl alcohol, petroselinyl alcohol, linolyl alcohol, linolenyl alcohol, behenyl alcohol and/or erucyl alcohol. Preference is given to using ring-opening products of hexadecene and/or octadecene epoxides with fatty alcohols having 16 to 18 carbon atoms. If polyols are used for the ring opening in place of fatty alcohols, they are, for example, the following substances: glycerol; alkylene glycols such as ethylene glycol, diethylene glycol, propylene glycol, butylene glycol, hexylene glycol and polyethylene glycols having an average molecular weight of 100 to 1000 Dalton; technical-grade oligoglycerol mixtures having a degree of self-condensation of 1.5 to 10 such as technical-grade diglycerol mixtures having a diglycerol content of 40 to 50% by weight; methyol compounds such as, in particular, trimethylolethane, trimethylolpropane, trimethylolbutane, pentaerythritol and dipentaerythritol; lower alkyl glucosides particularly those having 1 to 8 carbon atoms in the alkyl radical such as methyl glucoside and butyl glucoside; sugar alcohols having 5 to 12 carbon atoms such as sorbitol or mannitol, sugars having 5 to 12 carbon atoms such as glucose or sucrose, amino sugars such as glucamine.

Further Ingredients Customary in Shampoos or Hair Conditioners

Other useful ingredients which are customary in shampoos or hair conditioners are emulsifiers, consistency promoters, thickeners, polymers, lecithins, phospholipids, biogenic active ingredients, antidandruff agents, hydrotropes, film formers, preservatives, perfume oils and dyes.

Further Embodiments of the Composition

In one embodiment of the present invention the composition comprises
  at least one anionic surfactant, preferably a sodium alkyl ether sulfate having 12 to 14 carbon atoms and two ethylene oxide units, as ether component,
  optionally at least one cosurfactant which is different from the at least one surfactant, and which is a cocamidopropylbetaine,
  at least one cationic polymer,
  ethoxylated hydrogenated castor oils,
  ethoxylated coconut oil partial glycerides,
  trimethylpropane EO/PO trioleate,
  NaCl,
  optionally glycerol,
  optionally further ingredients customary in shampoos or hair conditioners, and
  water.

In one embodiment, the composition according to the present invention comprises
  10% to 20% by weight of the at least one surfactant,
  0% to 15% by weight of the at least one cosurfactant,
  0.1% to 5% by weight of the cationic polymer,
  0.06 to 3.5% by weight, preferably 0.12 to 2.1% by weight ethoxylated fatty acid glycerides, 0.06 to 2.5% by weight, preferably 0.12 to 1.5% by weight ethoxylated mono- and diglycerol esters,
0.03 to 0.5% by weight, preferably 0.06 to 0.3% by weight trimethylpropane EO/PO trioleate,
0.1 to 5% by weight, in particular 0.3 to 3% by weight, NaCl, optionally glycerol,
optionally comprises further ingredients customary in shampoos or hair conditioners, and
water to make up to 100% by weight.

In one embodiment, the composition according to the present invention comprises less than 2% by weight, in particular less than 1% by weight, in particular less than 0.5% by weight polysiloxanes.

In one embodiment, the composition according to the present invention comprises less than 2% by weight, in particular less than 1% by weight, in particular less than 0.5% by weight of substances which are emollients or waxes.

Intermediate

The present invention further provides an intermediate suitable for preparing the composition according to the invention, comprising
ethoxylated fatty acid glycerides,
ethoxylated mono- and diglycerol esters
trimethylpropane EO/PO trioleate,
optionally NaCl,
optionally water, and
optionally glycerol.

Here, the terms ethoxylated fatty acid glycerides, ethoxylated mono- and diglycerol esters and trimethylpropane EO/PO trioleate have the same meaning as in the context of the composition according to the invention and can be realized in particular in those embodiments which are realized in the embodiments of the composition according to the invention.

Proportions in the Intermediate

In one embodiment, the components of the intermediate ((a) ethoxylated fatty acid glycerides, (b) ethoxylated mono- and diglycerol esters, (c) trimethylpropane EO/PO trioleate) are present in the intermediate in a mass ratio of a:b:c=2-1:1-2:0.2-0.5, particularly 2:1:0.3.

The ethoxylated fatty acid glycerides present in the intermediate according to the invention are present in the intermediate according to the invention preferably in an amount of 12 to 70% by weight, in particular 40 to 66% by weight, in particular 55 to 56% by weight.

The ethoxylated mono- and diglycerol esters present in the intermediate according to the invention are present in the intermediate according to the invention preferably in an amount of 12 to 50% by weight, in particular 20 to 33% by weight, in particular 27 to 28% by weight.

The trimethylpropane EO/PO trioleate present in the intermediate according to the invention is present in the intermediate according to the invention preferably in an amount of 6 to 10% by weight, in particular 8 to 9% by weight.

The glycerol optionally present in the intermediate according to the invention is present in the intermediate according to the invention preferably in an amount of 3 to 5% by weight.

The water present in the intermediate according to the invention is present in the intermediate according to the invention preferably in an amount of 6 to 10% by weight, in particular 4 to 5% by weight.

Further Embodiments of the Intermediate

One embodiment of the present invention is the intermediate suitable for preparing the composition according to the invention, comprising
ethoxylated hydrogenated castor oils,
ethoxylated coconut oil partial glycerides,
trimethylpropane EO/PO trioleate,
optionally NaCl,
optionally water, and
optionally glycerol.

A further embodiment of the present invention is the intermediate suitable for preparing the composition according to the invention, comprising
12 to 70% by weight, preferably 40 to 66% by weight, ethoxylated fatty acid glycerides, preferably ethoxylated hydrogenated castor oils,
12 to 50% by weight, preferably 20 to 33% by weight, ethoxylated mono- and diglycerol esters, preferably ethoxylated coconut oil partial glycerides,
6 to 10% by weight trimethylpropane EO/PO trioleate,
optionally NaCl,
optionally water, and
optionally glycerol.

A further embodiment of the present invention is the intermediate suitable for preparing the composition according to the invention, comprising
55 to 56% by weight ethoxylated hydrogenated castor oil having 40 ethylene oxide units,
27 to 28% by weight ethoxylated coconut oil partial glycerides having 7 ethylene oxide units,
8 to 9% by weight trimethylpropane EO/PO trioleate having 120 ethylene oxide units (EO) and 10 propylene oxide units (PO),
optionally NaCl,
4 to 5% by weight water, and
3 to 5% by weight glycerol.

The intermediate is added to the composition according to the invention typically in an amount of 0.5 to 5% by weight, preferably 1 to 3% by weight.

Further Objects of the Invention

The present invention further relates to the use of the intermediate according to the invention for preparing the composition according to the invention.

The present invention further relates to a method for preparing the composition according to the invention comprising providing the intermediate according to the invention and bringing the intermediate into contact with the other constituents of the composition.

The present invention further relates to the use of the composition according to the invention for conditioning hair, preferably human hair.

The present invention further relates to the use of the composition according to the invention for improving the combability, preferably for improving the wet combability, of hair, preferably human hair. A particular embodiment of this use is given if the hair is damaged and hydrophilic.

EXAMPLES

Unless otherwise stated below, % refers to % by weight.
Unless otherwise stated below, RT or room temperature signifies 20° C.
EO signifies ethyleneoxy units.
Description of the branded products used in the examples below according to INCI:

| | |
|---|---|
| Texapon ® N 70 | Sodium Laureth Sulfate + 2 EO |
| Dehyton ® PK 45 | Cocamidopropyl Betaine |
| Polymer JR 400 | Polyquaternium-10 |
| Arlypon ® TT liquid | Trimethylolpropane + 120 EO/10 PO Random Trioleate |
| Cetiol ® HE | Coco, Mono- and Diglycerides + 7 mol EO |
| Eumulgin ® CO 40 | hydrogenated Castor Oil + 40 mol EO |
| Dehyquart ® CC7 BZ | Polyquaternium-7 |
| Dehyquart ® Guar N | Guar Hydroxypropyltrimonium Chloride |
| Dehyquart ® Guar TC | Guar Hydroxypropyltrimonium Chloride |
| Dehyquart ® Guar HP | Guar Hydroxypropyltrimonium Chloride |
| Euperlan ® PK 710 Benz | Glycol Distearate and Sodium Laureth Sulfate and Cocamide MEA |

Shampoos were prepared in accordance with the composition in % by weight specified in the following table.

| | Examples 12-278- | | | | |
|---|---|---|---|---|---|
| | 04 | 05 | 06 | 07 | 08 |
| Texapon ® N 70 | 15.70 | 15.70 | 15.70 | 15.70 | 15.70 |
| Dehyton ® PK 45 | 7.40 | 7.40 | 7.40 | 7.40 | 7.40 |
| Polymer ® JR 400 | 0.50 | 0.50 | 0.50 | 0.50 | 0.50 |
| Arlypon ® TT liquid | — | 0.30 | 0.30 | 0.30 | — |
| Cetiol ® HE | — | — | 1.0 | 1.0 | 1.0 |
| Eumulgin ® CO 40 | — | — | — | 2.0 | 2.0 |
| Parfum Cotton Touch | 0.20 | 0.20 | 0.20 | 0.20 | 0.20 |
| Na Benzoate | 0.50 | 0.50 | 0.50 | 0.50 | 0.50 |
| Citric acid 50% in water | 0.90 | 0.87 | 0.97 | 0.77 | 0.90 |
| NaCl | 0.70 | 0.70 | 0.70 | 0.70 | 0.70 |
| Water | 74.10 | 73.83 | 72.73 | 70.93 | 71.10 |
| pH | 4.73 | 4.70 | 4.74 | 4.70 | 4.87 |
| Viscosity at RT [mPas]* | 5000 | 25000 | 36000 | 4400 | 600 |
| WC %** | 87 +− 10 | 72 +− 4 | 60 +− 9 | 39 +− 4 | 45 +− 5 |

*The viscosity of the resulting shampoos was measured by means of a Brookfield viscometer of type RTV DV-II at 20° C.
**The wet combability in % of the reference value (WC %) was determined according to the following method.

The measurements were conducted in each case on 10 hair strands in an automated system for determining the wet combability.

The hair strands (12 cm/1 g) from HIP were pretreated in an automated hair treatment system according to the following steps:

30 min cleansing with 6% sodium lauryl ether sulfate, pH 6.5, then intensive rinsing of the hair, 20 min bleaching with a 5% hydrogen peroxide solution, pH 9.4 (adjusted with ammonium hydroxide solution), then intensive rinsing of the hair, 30 min drying in a stream of air at 68° C.

Directly prior to the blank measurement, the hair was swollen for 30 minutes in water and then rinsed for 1 minute in an automatic wet combing machine. In the automated system for determining the wet and dry combability, the combing forces were determined during 20 combings and the combability calculated by integrating the force-displacement curves measured. After the blank measurement, the hair was immediately treated with the formulation (0.25 g/g of hair). After 5 minutes contact time, the hair was rinsed with the automatic wet combing machine under standard conditions (38° C., 1 l/minute). The treatment and subsequent rinsing was repeated a second time. The comparative measurement (to the blank measurement) was then carried out. The measurements were conducted using the fine comb side of the natural rubber comb. The remaining combability per strand was calculated as follows:

remaining combability=combability before product treatment/combability after product treatment The remaining combability is the "WC %" value.

From the quotients of all 10 strands, the average and standard deviation was then determined.

From the above examples, the following conclusions could be drawn. Formulation −08 showed a significantly better WC compared to formulation −04. Further improvement of the wet combability could be achieved by using the thickener Arlypon® TT liquid (formulation −07). At the same time, the viscosity-reducing effect of the solubilizers could be canceled out.

The combination of the hydrophilic solubilizers plus thickeners which has been found to be advantageous was formulated into a product, the "hydrophilic conditioning compound". A small amount of water was added to the product for clarification. This compound was composed as follows:

composition of the "hydrophilic conditioning compound" (INCI nomenclature):

55.6% Eumulgin® CO 40: hydrogenated Castor Oil+40 mol EO 27.8% Cetiol® HE: Coco, Mono- and Diglycerides+7 mol EO 8.3% Arlypon® TT liquid: Trimethylolpropane+120 EO/10 PO−Random−Trioleate 8.3% demineralized water The conditioning effect (WC improvement) of the hydrophilic compounds could also be demonstrated when using further conditioning polymers in clear and pearlescent systems. The examples are shown in the following table (composition in % by weight).

| Examples 14-017- | 01 | 02 | 05 | 21 | 22 | 23 | 24 |
|---|---|---|---|---|---|---|---|
| Texapon ® N 70 | 14.30 | 14.30 | 14.30 | 14.30 | 14.30 | 14.30 | 14.30 |
| Dehyton ® PK 45 | 5.40 | 5.40 | 5.40 | 5.40 | 5.40 | 5.40 | 5.40 |
| Salcare ® SC 60 | 0.10 | — | — | 0.10 | — | — | — |
| Polymer JR 400 | — | 0.20 | — | — | 0.20 | — | — |
| Dehyquart ® Guar HP | — | — | — | — | — | 0.20 | — |
| Dehyquart ® Guar N | — | — | — | — | — | — | 0.20 |
| Dehyquart ® Guar TC | — | — | 0.20 | — | — | — | — |
| Euperlan ® PK 710 | — | — | — | 3.0 | 3.0 | 3.0 | 3.0 |
| Hydrophilic Compound | 2.0 | 2.0 | 2.0 | 2.0 | 2.0 | 2.0 | 2.0 |
| Parfum Cotton Touch | 0.50 | 0.50 | 0.50 | 0.50 | 0.50 | 0.50 | 0.50 |

| Examples 14-017- | 01 | 02 | 05 | 21 | 22 | 23 | 24 |
|---|---|---|---|---|---|---|---|
| Na Benzoate | 0.50 | 0.50 | 0.50 | 0.50 | 0.50 | 0.50 | 0.50 |
| Citric acid 50% in water | 0.72 | 0.70 | 0.78 | 0.84 | 0.77 | 0.82 | 0.75 |
| NaCl | 2.21 | 2.62 | 2.37 | 1.72 | 1.67 | 1.38 | 1.37 |
| Water | 74.27 | 73.78 | 73.95 | 71.64 | 71.66 | 71.90 | 71.98 |
| Viscosity (mPas) | 5000 | 6100 | 6300 | 6040 | 5680 | 5800 | 5400 |
| WC (%) | 58 | 63 | 64 | 51 | 64 | 47 | 66 |
| Standard deviation | 6 | 3 | 5 | 3 | 4 | 3 | 4 |
| DC (%) | 105 | | | | | 62 | |

Formulation -23 showed a considerable improvement in the wet combability in the case of particularly highly damaged hair (bleached 3 times). The WC of formulation -23 was 52% (+-4%) compared to the placebo formulation without the hydrophilic compound 101% (+-12%).

DC signifies dry combability. The comparison shows a significantly better value for example 23 compared to example 1.

Also variations in the composition of the hydrophilic conditioning compound showed similar results in the improvement in combability. The examples are shown in the following table (composition in % by weight).

|  | Examples 14-017- | | | |
|---|---|---|---|---|
|  | 29 | 30 | 31 | 32 |
| Texapon ® N 70 | 14.30 | 14.30 | 14.30 | 14.30 |
| Dehyton ® PK 45 | 5.40 | 5.40 | 5.40 | 5.40 |
| Polymer JR 400 | 0.20 | 0.20 | 0.20 | 0.20 |
| Dehyquart ® Guar TC | — | — | — | — |
| Hydrophilic compound (alternative 1) | 2.00 | — | — | — |
| Hydrophilic compound (alternative 2) | — | 2.00 | — | — |
| Hydrophilic compound (alternative 3) | — | — | 2.00 | — |
| Hydrophilic compound (alternative 4) | — | — | — | 2.00 |
| Parfum Cotton Touch | 0.50 | 0.50 | 0.50 | 0.50 |
| Na Benzoate | 0.50 | 0.50 | 0.50 | 0.50 |
| Citric acid 50% in water | 0.73 | 0.73 | 1.08 | 0.65 |
| NaCl | 2.50 | 2.23 | 1.56 | 1.18 |
| Water | 73.87 | 74.14 | 74.46 | 75.27 |
| WC (%) | 62 | 60 | 61 | 57 |
| Standard deviation | +-4.3 | +-4.3 | +-5.3 | +-3.3 |

| Hydrophilic compound alternative 1: | Hydrophilic compound alternative 2: |
|---|---|
| 8.3% Arlypon ® TT liquid | 8.3% Arlypon ® TT liquid |
| 55.6% Eumulgin ® HRE 40 | 55.6% Eumulgin ® HRE 40 |
| 27.8% Cetiol ® 767 | 27.8% Cremophor ® WO7 |
| 8.3% demineralized water | 8.3% demineralized water |

| Hydrophilic compound alternative 3: | Hydrophilic compound alternative 4: |
|---|---|
| 8.3% Arlypon ® TT liquid | 8.3% Arlypon ® TT liquid |
| 55.6% Eumulgin ® HRE 60 | 27.8% Eumulgin ® HRE 40 |
| 27.8% Cetiol ® HE | 55.6% Cetiol ® HE |
| 8.3% demineralized water | 8.3% demineralized water |

In experiments on the microbial stability of the intermediate (hydrophilic conditioning compound), a water content of 8.3% was found to be high in terms of water activity. In one variation, therefore, some of the water was replaced by glycerol. In this case, the 8.3% water was reduced to 4.3% water and 4% glycerol was added, whereby the water activity was reduced to within a microbially harmless range.

A modification to the advantageous properties of the intermediate with regard to its contribution to the conditioning effect of compositions produced therefrom by the partial exchange of water for glycerol is not to be expected.

A possible composition of the compound is therefore:

Eumulgin® CO 40 (55.6%): hydrogenated Castor Oil+40 mol EO

Cetiol® HE (27.8%): Coco, Mono- and Diglycerides+7 mol EO

Arlypon® TT liquid (8.3%): Trimethylolpropane+120 EO/10 PO–Random–Trioleate

Demineralized water (4.3%)

Glycerol (4.0%)

Further Examples

A feature of the composition according to the invention is the presence of NaCl. This ensures that the coacervate mechanism of anionic surfactant and cationic polymer is initiated in the dilution phase. In this case, the NaCl can be entrained with the cosurfactant (cocamidopropylbetaine for example which often, by virtue of the production process, often already comprises ca. 5-7.5% by weight NaCl) and/or can be added separately. The two examples which follow show a statistically relevant improvement in the wet combability as a function of the use of NaCl:

|  | Examples 14-017- | |
|---|---|---|
|  | 66 | 67 |
| Texapon ® N 70 | 20.00 | 20.00 |
| Polymer JR 400 | 0.20 | 0.20 |
| Hydrophilic Compound | 3.30 | 3.30 |
| Parfum Cotton Touch | 0.50 | 0.50 |
| Na Benzoate | 0.50 | 0.50 |
| Citric acid 50% in water | 0.60 | 0.75 |
| NaCl | — | 1.85 |
| Water | 74.90 | 73.78 |
| WC (%) | 88 | 75 |
| Standard deviation | 10 | 8 |

The invention claimed is:

1. A composition suitable as a shampoo or hair conditioner, comprising
   at least one surfactant,
   optionally at least one cosurfactant which is different from the at least one surfactant,
   at least one cationic polymer,
   an ethoxylated fatty acid glyceride,
   ethoxylated mono- and diglycerol esters,
   trimethyolpropane EO/PO trioleate,
   NaCl,
   optionally glycerol,
   optionally further ingredients customary in shampoos or hair conditioners, and
   water;
   wherein:
     the composition is free from fatty acid alkanolamides,
     the ethoxylated fatty acid glyceride is present in a mass amount A,
     the ethoxylated mono- and diglycerol esters are present in a mass amount B,
     the trimethyolpropane EO/PO trioleate is present in a mass amount C,
     a mass ratio A:B in the composition ranges from 2:1 to 1:2,
     a mass ratio B:C in the composition ranges from 2:1 to 10:1, and
     a mass ratio A:C in the composition ranges from 2:1 to 10:1.

2. The composition as claimed in claim 1, wherein said composition comprises
   10% to 20% by weight of the at least one surfactant,
   0% to 15% by weight of the at least one cosurfactant,
   0.1% to 5% by weight of the cationic polymer,
   0.06 to 3.5% by weight of the ethoxylated fatty acid glyceride,
   0.06 to 2.5% by weight ethoxylated mono- and diglycerol esters,
   0.03 to 0.5% by weight trimethyolpropane EO/PO trioleate,
   0.1 to 5% by weight, NaCl,
   optionally glycerol,
   optionally further ingredients customary in shampoos or hair conditioners, and
   water to make up to 100% by weight.

3. The composition as claimed in claim 1, wherein the cationic polymer is selected from the group consisting of a cationically modified cellulose derivative, PQ 10, PQ 67, a cationically modified guar derivative, guar hydroxypropyltrimonium chloride, a cationic homo- or copolymer based on acrylamide, a cationic homo- or copolymer based on vinyl pyrrolidone, a cationic homo- or copolymer based on quaternized vinyl imidazole, and a cationic homo- or copolymer based on methacrylates.

4. The composition as claimed in claim 1, wherein the at least one surfactant is an anionic surfactant.

5. The composition as claimed in claim 1, wherein the at least one surfactant is selected from the group consisting of a sulfate, an ethoxylated sulfate, a sulfonate, an alkyl polyglycoside, a derivative of an alkyl polyglycoside, a betaine, an amphoacetate, a glutamate, a sulfosuccinate, a taurate, a glycinate, and an isethionate.

6. The composition as claimed in claim 1, wherein the composition comprises less than 2% by weight polysiloxanes.

7. The composition as claimed in claim 1, wherein the composition comprises less than 2% by weight of substances which are emollients or waxes.

8. A method for conditioning hair, the method comprising:
   applying a composition according to claim 1 to hair, thereby conditioning the hair.

9. A method for improving the combability of hair, the method comprising:
   applying a composition according to claim 1 to hair, thereby improving the combability of the hair.

10. The method of claim 8, wherein the hair is damaged and hydrophilic.

11. The composition as claimed in claim 2 comprising 0.3 to 3% by weight NaCl.

12. The method of claim 8 wherein the hair is human hair.

13. The method of claim 9 wherein the hair is human hair.

14. The method of claim 9 wherein the wet combability of the hair is improved.

15. The method of claim 9, wherein the hair is damaged and hydrophilic.

16. The composition of claim 1, wherein the at least one surfactant comprises an anionic surfactant present in an amount ranging from 10% to 20% by weight.

* * * * *